United States Patent [19]

Huber et al.

[11] Patent Number: 5,219,764
[45] Date of Patent: Jun. 15, 1993

[54] HAPTEN-BIOTIN CONJUGATES AND THEIR USE

[75] Inventors: Erasmus Huber, Unterfinning; Dietmar Zdunek, Munich; Christian Klein; Roland Schenk, both of Weilheim, all of Fed. Rep. of Germany

[73] Assignee: Boehringer Mannheim GmbH, Mannheim, Fed. Rep. of Germany

[21] Appl. No.: 683,284

[22] Filed: Apr. 10, 1991

[30] Foreign Application Priority Data

Apr. 10, 1990 [DE] Fed. Rep. of Germany ....... 4011601

[51] Int. Cl.$^5$ ................ G01N 33/536; G01N 33/541; C07D 495/04
[52] U.S. Cl. .................... 436/536; 436/500; 436/540; 436/544; 435/7.5; 548/304.1; 544/267; 562/447
[58] Field of Search .............. 435/7.5; 436/536, 500, 436/532, 533, 540, 543, 544, 822, 823; 530/367, 380, 402, 807; 548/303; 544/267; 562/447

[56] References Cited

U.S. PATENT DOCUMENTS

| 4,617,261 | 10/1986 | Sheldon, III et al. ............. 435/6 |
| 4,760,142 | 2/1988 | Primes et al. ................ 544/287 |
| 4,898,951 | 2/1990 | Symons ..................... 548/303 |

FOREIGN PATENT DOCUMENTS

| 0183901 | 11/1986 | European Pat. Off. . |
| 0310361 | 5/1989 | European Pat. Off. . |
| 0315317 | 10/1989 | European Pat. Off. . |
| 0349988 | 10/1990 | European Pat. Off. . |

OTHER PUBLICATIONS

Green et al Biochem J. (1971) 125, 781-791.
Harlow et al Chapter 14, pp. 591-592 in *Antibodies A Laboratory Manual* Cold Spring Harbor (1988).

*Primary Examiner*—Esther L. Kepplinger
*Assistant Examiner*—Lora M. Green
*Attorney, Agent, or Firm*—Felfe & Lynch

[57] ABSTRACT

Hapten-biotin conjugates in which the hapten is linked with biotin via a spacer, which has 26 to 40 atoms in its chain and contains at least 5 heteroatoms, are novel and are suitable, in particular for use in a competitive homogeneous immunoassay in which the agglutination which occurs in the reaction is evaluated by turbidimetric or nephelometric measurements.

6 Claims, No Drawings

HAPTEN-BIOTIN CONJUGATES AND THEIR USE

The invention concerns hapten-biotin conjugates and their use.

Many substances occur in body fluids and tissues, which are capable of binding to a specific binding partner but which themselves cannot trigger an immunological reaction and are therefore denoted haptens, which serve as parameters for certain diseases or for the state of health of the human body. Haptens include hormones, tumour markers and viral proteins among others. In addition most drugs whose determination is often necessary for monitoring drug treatment are grouped with the haptens. Since all these haptens only occur in very small amounts one uses methods based on immunoassays for their detection. There are many variants of this. The various immunological methods of determination may be classified into homogeneous and heterogeneous methods. A solid phase reaction is always involved in the heterogeneous methods in order to separate the bound fraction of the labelled components from the unbound. In this type of method the label can be easily determined. A disadvantage is, however, that the heterogeneous reaction takes a long time.

In the homogeneous method variant there is no separation of bound label and unbound label and, as a result, differentiation between bound and unbound label has to take place by other methods. There are different possibilities for this. Thus, conjugated enzymes to e.g., can be used as label which only then become enzymatically active when they are bound to the hapten or antigen to be determined or when they are activated by the substance to be determined. A further possibility is to use a fluorescent substance as label whose fluorescence is either shifted to another wavelength range by binding to the substance to be determined or its polarization is changed.

A particular disadvantage of these known methods is that the sample often contains components which interfere with the test, thus necessitating pretreatment of sample in order to remove these substances. In addition extensive optimization is necessary for each parameter, e.g. the enzymes must be modified in a way which depends on the parameter. In all these tests there are conflicting requirements for optimal differentiation and optimal sensitivity, since on the one hand the concentration of the particulate reagent should be limited in order to allow an adequate competitive reaction with the sample and on the other hand the particulate reagent should be highly concentrated and highly labelled in order to achieve an adequate signal change per unit time. The balance of these requirements leads to limited sensitivity and susceptibility to interference which can often only be eliminated by specific sample pre-treatment.

In order to solve these problems a homogeneous method of determination was suggested in EP-A 0 349 988 in which the sample solution is incubated with 3 receptors $R_1$, $R_2$ and $R_3$ of which $R_1$ and $R_2$ are capable of binding to one another and $R_3$ is capable of specific binding to the substance to be determined in which receptor $R_1$ is a conjugate of a partner of a specific binding pair P and a substance S which corresponds to the substance to be determined or is a derivative thereof or at least has an epitope of the substance to be determined, $R_2$ is a receptor which has at least two binding sites for the specific binding partner and $R_3$ is a receptor which has at least two binding sites of which at least one binds specifically to an epitope of the substance to be determined or of S. On incubation of the sample solution with these three receptors the substance to be detected competes with the receptor $R_1$ for binding to receptor $R_3$ and receptor $R_2$ binds with receptor $R_1$. An agglutination results which can be monitored photometrically only when receptors $R_1$, $R_2$ and $R_3$ bind. Binding of the substance to be determined to receptor $R_3$ prevents the agglutination and therefore the agglutination is an indirect measure for the content of the substance to be detected. This method is suitable for the detection of immunologically active substances such as antigens, antibodies and haptens. For the detection of haptens a conjugate of a partner of a specific binding pair and of a hapten is used as receptor $R_1$ In a particularly advantageous embodiment a conjugate of biotin and substance S is used as receptor $R_1$, latex coated with streptavidin is used as receptor $R_2$ and an antibody capable of binding to the substance to be detected is used as receptor $R_3$. The biotin-hapten conjugate binds via the biotin moiety to the streptavidin-coated latex. The antibody can bind to the hapten-biotin conjugate via the hapten moiety. If two complexes of streptavidin-coated latex and biotin-hapten conjugate now bind to the antibody a turbidity then occurs which can be evaluated. The turbidity in this process occurs the more slowly the larger the amount to be analyzed and the smaller the solvation of the conjugate.

Thus, conjugates of a hapten and biotin have to be provided for the detection of haptens in the type of methods described above. Hapten-biotin conjugates have in fact been known for a long time. Thus in EP-A 35 317 a so-called bidentate conjugate is described which consists of an immunologically active molecule and a specific binding partner which are linked together via a spacer. Investigations have been carried out in order to determine the extent to which the length of the spacer has an effect on the properties of the conjugate. As a result it was established in this literature reference that the conjugates have an optimal effectiveness when the spacer length is more than 22.2 Å, which corresponds approximately to a chain length of 18 atoms, but that, on the other hand, a chain length of more than 20 atoms reduces the sensitivity. In addition it is stated that the presence of more than 5 heteroatoms is disadvantageous. However, absolutely satisfactory results have not yet been achieved with these conjugates.

Thus the object of the present invention was to provide hapten-biotin conjugates which are suitable for homogeneous immunoassay methods which have an improved sensitivity and with which the rate of the reaction is increased.

This object is achieved by using hapten-biotin conjugates which are characterized in that the hapten is linked with biotin via a spacer which has 26 to 40 atoms in the chain and contains at least 5 heteroatoms.

Surprisingly it was established that by using the hapten-biotin conjugates as defined according to the present invention a substantial improvement in the signal can be achieved compared to known conjugates, the occurrence of non-specific binding can be reduced by an improved solvation, the rate of the reaction can be increased and the test performance improved.

According to the present invention hapten-biotin conjugates are provided in which the hapten and the biotin molecule are linked via a spacer which has a chain length of 26 to 40 atoms and contains at least 5 heteroatoms.

The heteroatoms of the spacer can be heteroatoms which occur in organic molecules such as nitrogen, oxygen, sulphur, phosphorus etc. The spacer preferably contains nitrogen and oxygen atoms as heteroatoms. The number of heteroatoms must be at least 5. A higher proportion of heteroatoms is advantageous and the proportion of heteroatoms can be so large that every third atom in the spacer is a heteroatom. Thus a polyethylene oxide of the stated chain length can for example be used as the spacer.

The spacer length is in the range of 26 to 40 atoms in which only the atoms which are present in the chain are counted. Particularly advantageous results are obtained with spacers which have more than 30 atoms.

The production of the conjugates according to the present invention can either take place by reacting the hapten and the biotin with a bi-functional spacer molecule in which functional groups present on the hapten and in the biotin molecule react with the functional groups of the spacer molecule. Another possibility is to derivatize the hapten/or the biotin molecule and to subsequently react the derivative again, if desired, with a spacer molecule. The derivatives and spacer molecules are in turn selected so that a spacer of the desired length and with the desired number of heteroatoms is formed.

The derivatization of hapten and biotin is carried out in a known manner. Homo- or heterobifunctional linkers such as dicarboxylic acid, diamines, amino acids, mercaptocarboxylic acids and halogencarboxylic acids are suitable as the spacer. Spacers are preferably used which are synthesized from succinate, glutarate, suberate, ethylene diamine, propylene diamine, 1,8 diamino-3,6-dioxaoctane, 1,12-diamino-4,9-dioxadodecane, aminobutyric acid, aminocaproic acid, thioglycolic acid, thiopropionic acid, bromoacetic acid and/or iodoacetic acid. These synthetic building blocks must be combined in such a way that a spacer is formed which has the desired length and the desired number of heteroatoms.

An improved solvation is achieved with the hapten-biotin conjugates according to the present invention which leads to a shortened reaction time and thus to an increase in the capacity.

A further subject matter of the invention is the use of hapten-biotin conjugates in a competitive homogeneous immunoassay in which the agglutination which occurs in the reaction is evaluated by turbidimetric or nephelometric measurements.

The invention is elucidated by the following examples. The detection of the substances on the TLC plates is carried out by fluorescent quenching at 254 nm (silica gel $F_{254}$, Merck Company, No. 5748 or silica gel RP-18, Merck Company, No. 15685) or, in the case of compounds containing biotin, by spraying with $H_2SO_4$/4-dimethylamino-cinnamaldehyde. Mixture A/B 1/1 (v/v):

A) 2% $H_2SO_4$ in ethanol
B) 0.2% 4-dimethylamino-cinnamaldehyde in ethanol in which it was subsequently dried at 100° C. for 10 minutes.

EXAMPLE 1

Instructions for producing
5-(1-methylxanthin-3-yl)-pentanoic
acid-N-hydroxysuccinimide ester
(theopylline-3-cb-NHS)

1.a) 1-methyl-7-(pivaloyloxymethyl)xanthine 83 g 1-methylxanthine (0.5 mol, Aldrich Company, No. 28,098-4) is dissolved in 3.5 l of absolute DMF and 55 g anhydrous sodium carbonate is added. Subsequently 80 ml pivalic acid chloromethylester (Aldrich Company, No. 14, 118-6) in 300 ml absolute DMF are added dropwise within 30 minutes while stirring at 20° C.. After 48 hours reaction time it is aspirated over a nutsch filter and the filtrate is concentrated by evaporation in a high vacuum. The oily residue is digested with 500 ml diisopropylether until the product hardens and it is subsequently aspirated off. The solid is taken up in 500 ml chloroform, insoluble components are filtered off and the solution is concentrated by evaporation. The residue is digested with ca. 250 ml petroleum ether, the solid product is aspirated and dried in a desiccator.

Yield: 24.8 g (18% of the theoretical yield).
TLC: silica gel, acetic ester; $R_f = 0.58$.

1.b) 3-ethyloxycarbonylbutyl-1-methyl-7-(pivaloyloxymethyl)-xanthine 22.4 g (80 mmol) of the compound obtained under 1a) is dissolved in 300 ml absolute DMF and 17 g (160 mmol) anhydrous sodium carbonate and 33.6 g (=28 ml, 160 mmol) 5-bromopentanoic acid ethylester are added. This is stirred for 3 days at 20° C., then diluted with 3 l acetic ester, the solution is filtered and washed three times with 1 l water each time. The solution is dried with 100 g anhydrous sodium sulphate and the solvent is drawn off in a rotary evaporator. The remaining oily product can be used in this form for the next step.

Yield: 44 g viscous oil (contains large amounts of solvent).
TLC: silica gel, acetic ester; $R_f = 0.75$.

1.c) 3-carboxybutyl-1-methylxanthine (theophylline-3-cb)

The entire 44 g of the oily product obtained under 1b) are stirred under reflux in 2.8 l 2n NaOH for 2 hours. Afterwards it is cooled and the pH of the solution is adjusted to 5 with concentrated HCl. The product which precipitates in this process is aspirated, washed with water and dried under calcium chloride in a desiccator.

Yield: 10.6 g (50% of the theoretical yield).
TLC: silica gel, acetic ester/methanol 9/1 (v/v); $R_f = 0.37$.

1.d) 5-(1-methylxanthin-3-yl)pentanoic acid-N-hydroxysuccinimide ester (theophylline-3-cb-NHS)

5.3 g (20 mmol) of the theophylline carboxylic acid obtained under 1c) are dissolved in 150 ml absolute DMF and 2.76 g (24 mmol) N-hydroxysuccinimide and 4.95 g (24 mmol) dicyclohexylcarbodiimide are added. This is stirred for 24 hours at 20° C., afterwards the precipitated dicyclohexyl urea is aspirated, the filtrate is concentrated in a vacuum and dissolved again in 100 ml DMF. After filtration the solution is again concentrated in a vacuum and the residue is digested with 100 ml isopropanol. The solid product is aspirated and dried in a desiccator.

Yield: 6.0 g colourless, finely-crystalline powder (83% of the theoretical yield).

TLC: silica gel RP-18, nitromethane/ethanol 9/1 (v/v); $R_f = 0.82$.

EXAMPLE 2

Production of theophylline-3-cb-NH-NH-biotin 72.7 mg (0.2 mmol) theophylline-3-cb-NHS from Example 1 are dissolved in 20 ml absolute DMF and 77.5 mg (0.3 mmol) biotin hydrazide (Sigma Chemie Company, No. B7639) and 100 μg 4-(N,N-dimethylamino)pyridine (Merck Company, No. 820499) are added. This is stirred for 4 days at 20° C., then the solvent is removed in a high vacuum and the semi-solid residue is digested with ca. 5 ml methanol. The solid product is aspirated and dried with a high vacuum pump.

Yield: 66 mg colourless powder (65% of the theoretical yield).

TLC: silica gel, chloroform/methanol 2/1 (v/v); $R_f = 0.6$.

EXAMPLE 3

Production of theophylline-3-cb-1,8-diamino-3,6 dioxaoctane-biotin 182 mg (0.5 mmol) theophylline-3-cb-NHS from Example 1 are dissolved in 15 ml absolute DMF and stirred for 16 hours at 20° C. together with 206 mg (0.55 mmol) biotin-1,8-diamino-3,6-dioxaoctane (Biotin-DADOO) (Boehringer Mannheim Company, No. 1112 074). The solvent is then removed in a high vacuum and the residue is recrystallized from a small volume of methanol/chloroform 1/1 (v/v). The product is dried with a high vacuum pump.

Yield: 128 mg colourless, finely-crystalline powder (41% of the theoretical yield).

TLC: silica gel, chloroform/methanol 2/1 (v/v); $R_f = 0.57$.

EXAMPLE 4

Theophylline-3-cb-DADOO-ε-amino capionic acid-biotin 4.a) Biotin-X-DADOO 7.33 ml (50 mmol) 1,8-diamino-3,6-dioxaoctane (DADOO, Merck Company, No. 818116) are dissolved in 45 ml dioxane/0.1 m potassium phosphate buffer, pH 8.5 2/1 (v/v). While stirring at 20° C. a solution of 1.14 g (2.5 mmol) biotin-ε-aminocaproic acid-N-hydroxysuccinimide ester (Boehringer Mannheim Company, No. 1003 933) in the same solvent mixture is added dropwise during the course of 30 min. It is allowed to stir for a further 5 hours, then the solution is concentrated and the oily residue is dissolved in a small volume of methanol. While stirring vigorously 200 ml acetic ester are allowed to flow in whereby a whitish-yellow precipitate forms. It is aspirated, the precipitate is dissolved in as small a volume as possible of methanol/ammonia 9/1 (v/v) and it is purified over a silica gel column (5×30 cm), eluent methanol/ammonia 9/1 (v/v). The appropriate fractions are combined, concentrated by evaporation and the solid product is dried with a high vacuum pump.

Yield: 730 mg colourless powder (60% of the theoretical yield).

TLC: silica gel, methanol/ammonia 9/1 (v/v); $R_f = 0.46$.

4.b) Theophylline-3-cb-DADOO-ε-amino capronic acid-biotin 182 mg (0.5 mmol) theophylline-3-cb-NHS from Example 1 are dissolved in 20 ml absolute DMF and 245 mg (0.5 mmol) biotin-X-DADOO and 69 μl (0.5 mmol) triethylamine are added. This is stirred for 16 hours at 20° C., the solvent is then evaporated off in a vacuum and the product is purified by chromatography on a silica gel column (2.8×33 cm), eluent: chloroform/methanol 2/1 (v/v). The appropriate fractions are combined, the solvent is removed in a vacuum and the residue is digested with 20 ml diisopropylether. The solid product is dried over CaCl$_2$ in a desiccator.

Yield: 215 mg colourless powder (58% of the theoretical yield).

TLC: silica gel, chloroform/methanol 2/1 (v/v); $R_f = 0.60$.

EXAMPLE 5

Theophylline-3-cb-DADOD-ε-amino capronic acid-biotin 5.a) Theophylline-3-cb-DADOD 4.24 ml (20 mmol) 1,12-diamino-4,9-dioxadodecane (DADOD, Aldrich Company, No. 22,744-7) are dissolved in 10 ml absolute DMF and a solution of 363 mg (1 mmol) theophylline-3-cb-NHS from Example 1 in 20 ml absolute DMF are added dropwise during the course of 30 minutes. After a few minutes a flocculent precipitate forms. It is allowed to stir for a further 3 hours at 20° C., then it is filtered and the filtrate is concentrated in a vacuum. It is digested with 50 ml acetic ester, the solvent is decanted and the residue is dissolved in a small volume of DMF. The solution is allowed to flow into 50 ml acetic ester while stirring vigorously. The crude product which precipitates in this process is aspirated and purified by chromatography on a silica gel column (5×35 cm), eluent: chloroform/methanol/ammonia 6/3/1 (v/v/v). The appropriate fractions are combined, the solvent is removed in a vacuum and the remaining product is lyophilized from water. It is dried in a desiccator over CaCl$_2$.

Yield: 240 mg colourless powder (53% of the theoretical yield).

TLC: silica gel, chloroform/methanol/ammonia 6/3/1 (v/v/v); $R_f = 0.42$.

5.b) Theophylline-3-cb-DADOD-X-biotin 225 mg (0.5 mmol) theophylline-3-cb-DADOD are dissolved in 40 ml absolute DMF and 227 (0.5 mmol) biotin-ε-aminocaproic acid-N-hydroxysuccinimide ester are added. After addition of 69 μl (0.5 mmol) triethylamine it is allowed to stir for 6 hours at 20° C.. The solvent is removed in a high vacuum, the residue is dissolved in as small a volume as possible of chloroform/methanol 1/1 (v/v) and loaded onto a silica gel column (5×35 cm). It is eluted with chloroform/methanol 2/1 (v/v). The appropriate fractions are combined, the solvent is removed in a vacuum and theophylline-3-cb-DADOD-X-biotin is lyophilyzed from water.

Yield: 310 mg colourless powder (78% of the theoretical yield).

TLC: silica gel, chloroform/methanol 2/1 1 (v/v); $R_f = 0.54$;

EXAMPLE 6

Theophyllin 3-cb-DADOO-succ-DADOO-biotin 6.a) Biotin-DADOO-succ 1.5 g (4 mmol) biotin-DADOO are dissolved in 30 ml pyridine and 800 mg (8 mmol) succinic acid anhydride are added. After addition of 0.1 mg 4-(N,N-dimethylamino)-pyridine it is allowed to stir for 1 day at 20° C. Subsequently the solvent is removed in a high vacuum. The residue is digested with 20 ml acetic ester and aspirated. It is washed with ca. 20 ml acetic ester and the product is dried in a desiccator over $CaCl_2$.

Yield: 1.4 g colourless, finely crystalline powder (74% of the theoretical yield).

TLC: silica gel RP-18, isopropanol/water/glacial acetic acid 85/14/1 (v/v/v); Rf=0.74.

6.b) Biotin-DADOO-succ-DADOO 238 mg (0.5 mmol) biotin-DADOO-succ are dissolved in 25 ml absolute DMF and 57 mg (0.5 mmol) N-hydroxysuccinimide and 69 μl (0.5 mmol) 2-(4-morpholinyl)-ethylisocyanide (Merck Company, No. 818649) are added. This is stirred for 30 min at 20° C., then 1.5 ml (10 mmol) 1,8-diamino-3,6-dioxaoctane (DADOO, Merck Company, No. 818,116) and a further 57 mg N-hydroxysuccinimide and 69 μl 2-(4-morpholinyl)ethylisocyanide) are added. The solution is stirred for a further 16 hours, then the solvent is removed in a high vacuum and the product is purified by chromatography on a silica gel column (5×60 cm), eluent: chloroform/methanol/ammonia 6/3/1 (v/v/v). The appropriate fractions are combined, the solvent is removed and the residue is digested with 10 ml acetic ester. The solid product is aspirated and dried with a high vacuum pump.

Yield: 195 mg colourless powder (65% of the theoretical yield).

TLC: silica gel, chloroform/methanol/ammonia 6/3/1 (v/v/v); $R_f$=0.54.

6.c) Theophylline-DADOO-succ-DADOO-biotin 151 mg (0.25 mmol) biotin-DADOO-succ-DADOO are dissolved together with 91 mg (0.25 mmol) theophylline-3-cb-NHS from Example 1 in 10 ml absolute DMF and 35 μl (0.25 mmol) triethylamine are added. This is stirred for 4 days at 20° C., then the solvent is removed in a high vacuum and the product is isolated by column chromatography on a silica gel column (3.5×40 cm), eluent: chloroform/methanol 2/1 (v/v). The appropriate fractions are combined, the solvent is removed in a vacuum and the product is dried for at least 6 hours with a high vacuum pump.

Yield: 105 mg colourless, viscous oil (49% of the theoretical yield).

TLC: silica gel, chloroform/methanol 2/1 (v/v); $R_f$=0.36.

EXAMPLE 7

DETERMINATION OF THEOPHYLLINE

Reagents

Reagent 1, consisting of 0.1% by weight streptavidin latex (produced according to EP-A 0 349 988).

Reagent 2, consisting of $1.5 \times 10^{-6}$ mol/l monoclonal antibodies against theophylline and $4.5 \times 10^{-7}$ mol/l conjugate of theophylline and biotin (produced according to Example 6).

3 μl sample is added to 30 ml reagent 2 for 37° C. and incubated for 5 min. Subsequently 500 μl reagent 1 streptavidin-latex is added and the change in absorbance is determined within 4.2 min. Table 1 shows the calibration values obtained using aqueous theophylline solutions as samples.

EXAMPLES 8

Determination of T4 thyroxin

Reagents

Reagent 1, consisting of 100 mmol/l barbiturate buffer pH 8.5, 2% by weight dextran sulphate, 0.02% by weight streptavidin-latex (produced according to EP-A 0 349 988) $4 \times 10^{-8}$ mol/l polyclonal antibodies (IgG against T4).

Reagent 2, consisting of $4 \times 10^{-8}$ mol/l conjugate of T4 and biotin, produced analogous to Example 2 in which T4-(tert.-butyloxycarbonyl)-NHS (Boehringer Mannheim GmbH) is used instead of theophylline-3cb-NHS.

5 μl sample is added together with 235 μl reagent 1 at 37° C. and incubated for 5 min. Subsequently 20 μl reagent 2 is added and the change in absorbance over 2 min is determined at 405 nm. The calibration values according to Table 2 were obtained using serum standards.

TABLE 1

| Theophylline [mol/l] | ΔmA/4.2 min |
| --- | --- |
| $1.0 \times 10^{-5}$ | 461 |
| $2.6 \times 10^{-5}$ | 282 |
| $5.0 \times 10^{-5}$ | 145 |
| $10^{-4}$ | 40 |
| $2.0 \times 10^{-4}$ | 4 |

TABLE 2

| T4 [μg/dl] | ΔmA/2 min |
| --- | --- |
| 0.6 | 335.12 |
| 4.3 | 201.89 |
| 8.5 | 126.23 |
| 14.6 | 64.74 |
| 26.1 | 23.85 |

We claim:

1. A hapten-biotin conjugate consisting of a hapten linked to biotin via a spacer having a chain of from 30 to 36 atoms at least five of which are the heteroatoms selected from the group consisting of nitrogen, oxygen and combinations thereof.

2. The hapten-biotin conjugate of claim 1, wherein said hapten is a hormone or a drug.

3. The hapten-biotin conjugate of claim 1 wherein said spacer contains a carboxybutyl group, a 1,8-diamino-3,6-dioxaoctane or a 1,12-diamino-4,9-dioxadodecane.

4. The hapten-biotin conjugate of claim 1, designated theophylline-3-cb-DADOO-succ-DADOO-biotin.

5. The hapten-biotin conjugate of claim 1, wherein said hapten is thyroxine.

6. Method for determining a hapten in a sample comprising contacting said sample with (i) a hapten-biotin conjugate of claim 1, wherein the hapten of said conjugate is identical to the hapten to be determined, (ii) a receptor which specifically binds to both the hapten to be determined and said conjugate, and (iii) a receptor which specifically binds to said conjugate but not to said hapten to be determined under conditions wherein said hapten to be determined and said hapten-biotin conjugate compete for binding to (ii), and determining formation of an aggregate between (iii), and (ii), and (i) nephelometrically or turbidometrically as a measure of said hapten to be determined.

* * * * *

UNITED STATES PATENT AND TRADEMARK OFFICE
CERTIFICATE OF CORRECTION

PATENT NO. : 5,219,764
DATED : June 15, 1993
INVENTOR(S) : Erasmus Huber, et al.

It is certified that error appears in the above-indentified patent and that said Letters Patent is hereby corrected as shown below:

Col. 2, line 35: change "EP-A 35 317" to -- EP-A 315 317 --.

Signed and Sealed this

Thirtieth Day of August, 1994

Attest:

BRUCE LEHMAN

*Attesting Officer*  *Commissioner of Patents and Trademarks*